United States Patent
Granqvist et al.

(10) Patent No.: US 11,557,395 B2
(45) Date of Patent: Jan. 17, 2023

(54) PORTABLE EXERCISE-RELATED DATA APPARATUS

(71) Applicant: Polar Electro Oy, Kempele (FI)

(72) Inventors: Niclas Granqvist, Fleurier (CH); Tapio Kanniainen, Dulu (FI); Sami Karvonen, Travers (CH); Matti Korpela, Dulu (FI)

(73) Assignee: Polar Electro Oy, Kempele (FI)

( * ) Notice: Subject to any disclaimer, the term of this patent is extended or adjusted under 35 U.S.C. 154(b) by 659 days.

(21) Appl. No.: 16/693,444

(22) Filed: Nov. 25, 2019

(65) Prior Publication Data

US 2020/0205676 A1 Jul. 2, 2020

Related U.S. Application Data

(60) Continuation of application No. 14/683,387, filed on Apr. 10, 2015, now abandoned, which is a division of
(Continued)

(30) Foreign Application Priority Data

Dec. 18, 2009 (FI) .................................... 20096365

(51) Int. Cl.
*A61B 5/00* (2006.01)
*G16H 40/67* (2018.01)
(Continued)

(52) U.S. Cl.
CPC ........... *G16H 40/67* (2018.01); *A61B 5/0002* (2013.01); *A61B 5/0006* (2013.01);
(Continued)

(58) Field of Classification Search
None
See application file for complete search history.

(56) References Cited

U.S. PATENT DOCUMENTS 5,976,083 A * 11/1999 Richardson .......... G01C 22/006
482/901
6,808,473 B2 10/2004 Hisano et al.
(Continued)

FOREIGN PATENT DOCUMENTS

| EP | 2 000 083 A2 | 12/2008 |
| EP | 2 335 563 B1 | 5/2018 |
| WO | 2009/069163 A1 | 6/2009 |

OTHER PUBLICATIONS

Office Action received for Finnish Patent Application Serial No. 20096365 dated Oct. 11, 2010, 13 pages (Including English Translation).
(Continued)

*Primary Examiner* — Michael R Bloch
(74) *Attorney, Agent, or Firm* — FisherBroyles, LLP (57) ABSTRACT

A portable apparatus includes an exercise-measurement circuitry that measures exercise-related measurement data related to a user carrying out an exercise, a communication circuitry configured to provide the portable apparatus with wireless communication capability, and a processing circuitry configured to a perform operations. The operations include receiving the exercise-related measurement data from the exercise-measurement circuitry, receiving configuration data from an external user interface apparatus over a bidirectional wireless communication connection established through the communication circuitry and capable of transferring payload data to both directions, processing the exercise-related measurement data according to the received exercise-related parameters in order to obtain advanced exercise-related data, and communicating the advanced exercise-related measurement data to the user interface apparatus over the bidirectional wireless communication connection.

14 Claims, 2 Drawing Sheets

Related U.S. Application Data application No. 12/961,575, filed on Dec. 7, 2010, now abandoned.

(51) Int. Cl.

| | | |
|---|---|---|
| *A61B 5/024* | (2006.01) | |
| *A63B 24/00* | (2006.01) | |
| *A61B 5/11* | (2006.01) | |
| *G06F 3/16* | (2006.01) | |
| *G10L 19/00* | (2013.01) | |
| *G16H 20/30* | (2018.01) | |
| *G16H 40/40* | (2018.01) | |
| *A61B 5/0205* | (2006.01) | |
| *A63B 69/00* | (2006.01) | |
| *A63B 71/06* | (2006.01) | |
| *A61B 5/0245* | (2006.01) | |

(52) U.S. Cl.
CPC ...... *A61B 5/02055* (2013.01); *A61B 5/02438* (2013.01); *A61B 5/11* (2013.01); *A61B 5/1123* (2013.01); *A61B 5/4875* (2013.01); *A61B 5/7278* (2013.01); *A61B 5/7475* (2013.01); *A63B 24/0062* (2013.01); *G06F 3/165* (2013.01); *G10L 19/00* (2013.01); *G16H 20/30* (2018.01); *G16H 40/40* (2018.01); *A61B 5/024* (2013.01); *A61B 5/0245* (2013.01); *A61B 5/02405* (2013.01); *A63B 69/0028* (2013.01); *A63B 2024/0065* (2013.01); *A63B 2024/0068* (2013.01); *A63B 2024/0071* (2013.01); *A63B 2071/0625* (2013.01); *A63B 2071/0663* (2013.01); *A63B 2220/12* (2013.01); *A63B 2220/20* (2013.01); *A63B 2220/22* (2013.01); *A63B 2220/30* (2013.01); *A63B 2220/40* (2013.01); *A63B 2220/56* (2013.01); *A63B 2220/58* (2013.01); *A63B 2220/72* (2013.01); *A63B 2220/836* (2013.01); *A63B 2225/50* (2013.01); *A63B 2230/04* (2013.01); *A63B 2230/06* (2013.01); *A63B 2230/50* (2013.01); *A63B 2244/20* (2013.01)

(56) References Cited

U.S. PATENT DOCUMENTS

| | | |
|---|---|---|
| 7,018,339 B2 | 3/2006 | Birnbaum et al. |
| 7,717,827 B2 | 5/2010 | Kurunmäki et al. |
| 8,188,868 B2 | 5/2012 | Case, Jr. |
| 2003/0004424 A1 | 1/2003 | Birnbaum et al. |
| 2003/0073911 A1 | 4/2003 | Yoshimura et al. |
| 2004/0014567 A1* | 1/2004 | Mendel ............... G16H 20/30 482/8 |
| 2004/0122333 A1 | 6/2004 | Nissila |
| 2004/0162035 A1 | 8/2004 | Pertersen et al. |
| 2005/0176461 A1 | 8/2005 | Bozzone et al. |
| 2005/0266961 A1 | 12/2005 | Shum et al. |
| 2006/0063980 A1 | 3/2006 | Hwang et al. |
| 2006/0064037 A1 | 3/2006 | Shalon et al. |
| 2006/0136173 A1* | 6/2006 | Case, Jr. ............ A63B 24/0003 702/182 |
| 2007/0027000 A1 | 2/2007 | Shirai et al. |
| 2007/0113725 A1* | 5/2007 | Oliver ..................... G10H 1/40 84/612 |
| 2007/0113726 A1* | 5/2007 | Oliver ..................... G10H 1/40 84/615 |
| 2007/0123391 A1 | 5/2007 | Shin et al. |
| 2007/0142715 A1 | 6/2007 | Banet et al. |
| 2007/0208233 A1 | 9/2007 | Kovacs |
| 2008/0096726 A1 | 4/2008 | Riley et al. |
| 2008/0125288 A1 | 5/2008 | Case |
| 2008/0146968 A1 | 6/2008 | Hanawaka et al. |
| 2008/0153671 A1 | 6/2008 | Ogg et al. |
| 2008/0164979 A1 | 7/2008 | Otto |
| 2008/0190202 A1 | 8/2008 | Kulach et al. |
| 2008/0214360 A1 | 9/2008 | Stirling et al. |
| 2009/0009342 A1 | 1/2009 | Karjalainen |
| 2009/0047645 A1 | 2/2009 | Dibenedetto et al. |
| 2009/0093341 A1* | 4/2009 | James ............... A63B 24/0062 482/1 |
| 2010/0292050 A1 | 11/2010 | Dibenedetto et al. |
| 2011/0152695 A1 | 6/2011 | Granqvist et al. |
| 2015/0216427 A1 | 8/2015 | Granqvist et al. |

OTHER PUBLICATIONS

Extended European Search Report received for EP Patent Application Serial No. 10195134.1 dated Apr. 5, 2011, 7 pages.
Non-Final Office Action received for U.S. Appl. No. 12/961,575 dated Apr. 25, 2013, 34 pages.
Final Office Action received for U.S. Appl. No. 12/961,575 dated Nov. 6, 2013, 25 pages.
Non-Final Office Action received for U.S. Appl. No. 12/961,575 dated Apr. 22, 2014, 50 pages.
Final Office Action received for U.S. Appl. No. 12/961,575 dated Dec. 18, 2014, 41 pages.
Non-Final Office Action received for U.S. Appl. No. 12/961,575 dated Jul. 7, 2015, 48 pages.
Final Office Action received for U.S. Appl. No. 12/961,575 dated Nov. 4, 2015, 66 pages.
Non-Final Office Action received for U.S. Appl. No. 12/961,575 dated Jul. 5, 2016, 53 pages.
Final Office Action received for U.S. Appl. No. 12/961,575 dated Mar. 10, 2017, 55 pages.
Non-Final Office Action received for U.S. Appl. No. 12/961,575 dated Oct. 2, 2017, 40 pages.
Final Office Action received for U.S. Appl. No. 12/961,575 dated Jun. 4, 2018, 29 pages.
Non-Final Office Action received for U.S. Appl. No. 12/961,575 dated Jan. 10, 2019, 32 pages.
Final Office Action received for U.S. Appl. No. 12/961,575 dated Jul. 25, 2019, 33 pages.
Non-Final Office Action received for U.S. Appl. No. 14/683,387 dated Aug. 24, 2015, 31 pages.
Final Office Action received for U.S. Appl. No. 14/683,387 dated Mar. 23, 2016, 23 pages.
Non-Final Office Action received for U.S. Appl. No. 14/683,387 dated Jun. 30, 2016, 32 pages.
Final Office Action received for U.S. Appl. No. 14/683,387 dated Feb. 8, 2017, 30 pages.
Non-Final Office Action received for U.S. Appl. No. 14/683,387 dated Oct. 4, 2017, 31 pages.
Final Office Action received for U.S. Appl. No. 14/683,387 dated Jun. 1, 2018, 35 pages.
Non-Final Office Action received for U.S. Appl. No. 14/683,387 dated Jan. 10, 2019, 31 pages.
Final Office Action received for U.S. Appl. No. 14/683,387 dated Jul. 25, 2019, 35 pages.
Communication pursuant to Article 94(3) EPC received for EP Patent Application Serial No. 10195134.1 dated Jan. 27, 2012, 6 pages.
Communication pursuant to Article 94(3) EPC received for EP Patent Application Serial No. 10195134.1 dated Apr. 22, 2016, 5 pages.
Communication pursuant to Article 94(3) EPC received for EP Patent Application Serial No. 10195134.1 dated Jun. 29, 2017, 5 pages.
Intention to grant received for EP Patent Application Serial No. 10195134.1 dated Apr. 12, 2018, 59 pages.

* cited by examiner

PORTABLE EXERCISE-RELATED DATA APPARATUS

CROSS-REFERENCE TO RELATED APPLICATIONS

This application is a continuation of U.S. application Ser. No. 14/683,387 filed Apr. 10, 2015, which is a divisional of U.S. application Ser. No. 12/961,575 filed Dec. 7, 2010, which are incorporated by reference herein in their entireties.

BACKGROUND

Field

The invention relates to the field of biometric sensing and, particularly to processing measured exercise-related measurement data.

Description of the Related Art

Heart-rate monitors and other biometric sensors are commonly used by professional athletes as well as by conventional people practicing exercising. Heart-rate monitors and other biometric sensors typically provide a user with information enabling efficient workout. A typical heart-rate monitoring system includes a biometric sensor attached to the body of the user and configured to measure heart-rate of the user, to transmit the measured heart-rate to another device worn by the user (a wrist device, for example). The other device receives the heart-rate information from the biometric sensor, processes the heart-rate information, and displays the processed heart-rate information. The other device may also process the heart-rate so as to calculate more advanced information, such as energy expenditure and fitness parameters of the user.

US 2008/0190202 discloses a motion sensing apparatus to be attached to an object at an attachment position and comprising an accelerometer and a processing system. The processing system is operable to acquire acceleration measurements and to identify the attachment position of the motion sensing apparatus.

SUMMARY

According to an aspect of the present invention, there is provided an apparatus as specified in the claims.

According to another aspect of the present invention, there is provided a method as specified in the claims.

According to another aspect of the present invention, there is provided a system as specified in the claims.

According to yet another aspect of the present invention, there is provided a computer program product embodied on a computer-readable distribution medium and comprising program instructions for carrying out the above-mentioned method. According to another aspect, there is provided a computer-readable distribution medium or article of manufacture containing the above-mentioned computer program product.

Embodiments of the invention are defined in the dependent claims.

BRIEF DESCRIPTION OF DRAWINGS

Embodiments of the present invention are described below, by way of example only, with reference to the accompanying drawings, in which.

DETAILED DESCRIPTION

The following embodiments are exemplary. Although the specification may refer to "an", "one", or "some" embodiment(s) in several locations, this does not necessarily mean that each such reference is to the same embodiment(s), or that the feature only applies to a single embodiment. Single features of different embodiments may also be combined to provide other embodiments.

Figure 1:
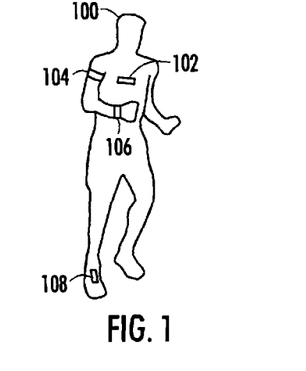
FIG. 1 illustrates a system for measuring and processing exercise-related information.

FIG. 1 illustrates an exemplary system for use to measure exercise-related data in order to monitor workout of a user 100. Referring to FIG. 1, the user may wear various devices that measure and process the exercise-related data. The user 100 is provided with the following equipment: a user interface apparatus in the form of a wrist unit 106, a heart rate sensor 102 worn on the chest of the user 100, an upper-arm-mounted positioning device 104, and a shoe-mounted stride sensor 108. Other accessories not illustrated in FIG. 1 include a bike sensor configured to measure the speed of a bike and/or a pedaling power of the user and a swimming sensor configured to monitor swimming motions, water pressure etc. The accessories 102, 104, 108 communicate wirelessly with the wrist device 106. Various accessories may be flexibly used as needed, i.e. all of them are not necessarily needed all the time, or by all users, or in all use cases.

The user interface apparatus 106 comprises a user interface which may comprise a display, means for producing sound, a keyboard, and/or a keypad. The display may be a liquid crystal display, for example, but it may also be implemented by any appropriate technique. The display may also incorporate other user interaction means, such as touch input, or haptic feedback, i.e. the display may be a touch screen. The means for producing sound may be a loudspeaker or a simpler means, such as a piezo element, for producing beeps or other audio signals. The keyboard/keypad may comprise a complete (QWERTY) keyboard, a mere numeric keypad or only a few push buttons and/or rotary buttons. In addition, the user interface 106 may comprise other prior art user interface elements, for example various means for focusing a cursor (mouse, track ball, various arrow keys, touch sensitive area etc.) or elements enabling audio control. A parameter relating to the exercise may be shown on the user interface 106, on the display, for example. The user interface device 106 also comprises means for communicating with the accessory devices 102, 104, and 108, as described in greater detail below.

The heart rate sensor 102 is used for measuring the user's heart activity. The heart activity comprises heart rate and one or multichannel EKG (Electrocardiogram), for example. The heart activity sensor 102 may further measure other physiological parameters that can be measured from the user. There exist various wireless heart rate monitoring concepts where a heart rate sensor attached to the user's chest measures the user's heart activity and transmits associated heart activity data telemetrically to a heart rate receiver, such as the wrist device 106 attached to the user's wrist. The transmission of the heart activity data may utilize the principles of time division and/or packet transmission, for example. However, the heart-rate (and/or other biometric data) is conventionally only measured, and the measurement data is forwarded to the wrist device 106 for further processing.

The positioning device 104 receives external location information. The positioning device 104 may be a receiver of a global navigation satellite system. Such a system may be the Global Positioning System (GPS), the Global Navigation Satellite System (GLONASS), the Galileo Positioning System (Galileo), the Beidou Navigation System, or the Indian Regional Navigational Satellite System (IRNSS), for example. The positioning device 104 determines its location elements, such as longitude, latitude, and altitude, using signals transmitted from satellites orbiting the earth. Besides global navigation satellites, the positioning device 104 may also determine its location by utilizing other known positioning techniques. It is well known that by receiving radio signals from several different base stations, a mobile phone may determine its location. The positioning device 104 may utilize such schemes as well. In an embodiment of the invention, the positioning device 106 applies proprietary positioning methods based on optical or electromagnetic measurements.

The stride sensor 108 (or the swimming sensor) comprises one or more motion sensors measuring the movement of the user, a processing unit configured to process the measured motion data of the user and to transmit the processed data to the wrist device 106 over a wireless connection. The motion sensor actually measures its own motion based on acceleration measurement, for example, and converts the acceleration into an electric signal. The electric signal is converted into a digital format in an AD converter. Acceleration can be expressed by the unit of measurement g. One g is the acceleration caused to an object by earth's gravity. Accelerations between −2 and +2 g can usually be measured from human movement. Various techniques may be used for measuring acceleration. Piezo-resistor technology employs material whose resistance changes as it compresses. The acceleration of mass produces a force in a piezo resistor. If a constant current is supplied through the piezo resistor, its voltage changes according to the compression caused by acceleration. In piezo-electric technology, a piezo-electric sensor generates charging when the sensor is accelerated. In silicon bridge technology, a silicon chip is etched so that a silicon mass remains on it at the end of a silicon beam. If acceleration is directed to the silicon chip, the silicon mass focuses a force on the silicon beam, thus changing the resistance of the silicon beam. Micro-machined silicon technology is based on the use of a differential capacitor. Voice coil technology is based on the same principle as a microphone. Examples of suitable movement sensors include: Analog Devices ADXL105, Pewatron HW or VTI Technologies SCA series. The implementation of the accelerometer may also be based on other appropriate techniques, for example on a gyroscope integrated into a silicon chip or on a micro vibration switch incorporated into a surface mounting component.

In summary, the accessory apparatuses 102, 104, and 108 each comprise at least one measurement sensor which measures some aspect of the exercise. The accessory apparatuses 102, 104, and 108 may provide raw measurement data without further processing, as a conventional heart activity sensor does, or the accessory apparatuses may process the raw data before outputting it. In any case, conventional accessory apparatuses are hardwired to carry out a determined processing to the measured data which is very inflexible, i.e. their operational parameters are fixed and cannot be changed after the manufacturing process is complete.

Figure 2:
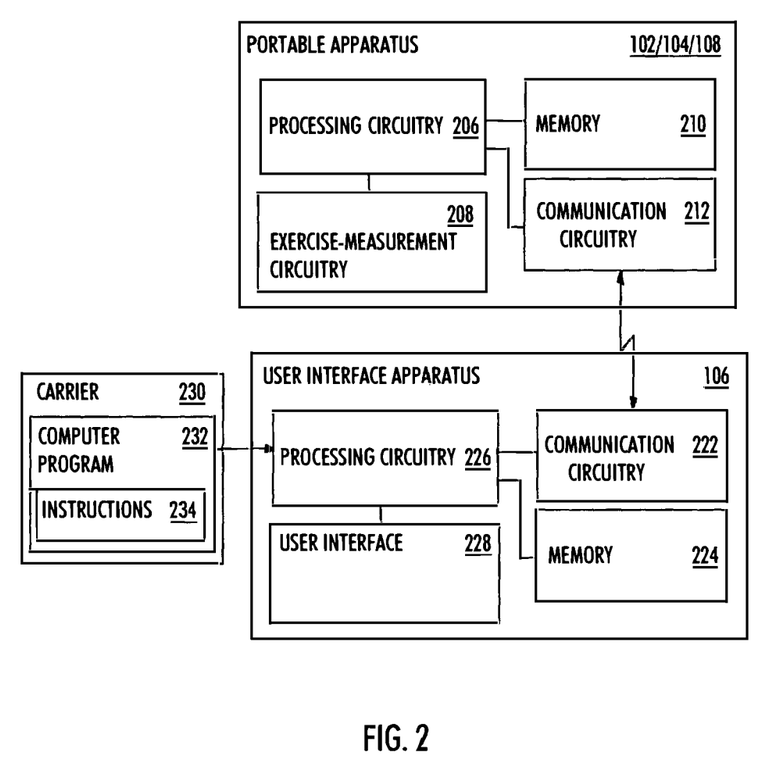
FIG. 2 is a block diagram of a system according to an embodiment of the invention.

FIG. 2 illustrates a generic block diagram of a system according to an embodiment of the invention. Referring to FIG. 2, an embodiment of the present invention provides a portable apparatus 102, 104, 108 comprising an exercise-measurement circuitry 208 configured to measure exercise-related measurement data related to a user carrying out an exercise, a communication circuitry 212 configured to provide the portable apparatus with bidirectional wireless communication capability, a processing circuitry 206, and a memory 210.

The exercise-related measurement data is measurement data characterizing an exercise.

In an embodiment of the invention, the exercise-related measurement data characterizes the user's heart activity. The exercise-related measurement data may comprise a part of a single or multi-channel ECG signal in the form of a character, such as timing instant, associated with a heart pulse.

In an embodiment of the invention, the exercise-related measurement data characterizes the user's motion. The exercise-related measurement data may comprise one or multi-dimensional acceleration values, one or multi-dimensional force values associated with degrees of freedom of motion, electric signals characters, such as voltage values, associated with the degrees of freedom of motion. The exercise-related measurement data may also comprise advanced motion information, such as speed and/distance values which are usually provided by commercially available motion detectors. The motion may further be presented other characteristics, such as by pulses and amplitudes associated with motion. The exercise-related measurement data may characterize motion of user's limbs, such as arms or leg, or it may present motion of user's overall motion.

The processing circuitry 206 is configured to receive the exercise-related measurement data from the exercise-measurement circuitry 208, to process the exercise-related measurement data in order to obtain advanced or "refined" exercise-related data, and to communicate with an external user interface apparatus 106 over the bidirectional wireless communication connection through the communication circuitry 212 so as to cause transmission of the processed exercise-related measurement data to the user interface apparatus 106 and to receive configuration data from the user interface apparatus 106. The configuration data may define how the exercise-related measurement data is processed and the type of the advanced exercise-related data, and the received configuration data may be stored in the memory 210 for use in the processing of the exercise-related measurement data. The portable apparatus may be any one of the accessory apparatuses 102, 104, and 108 or a hybrid apparatus comprising a plurality of different types of exercise-measurement circuitries, e.g. a heart-rate sensor, a motion sensor, and a positioning sensor.

Providing a bidirectional communication link between the portable apparatus 102, 104, 108 and the user interface apparatus 106 enables input of configuration data into the portable apparatus 102, 104, 108 carrying out the measurement. As a consequence, the portable apparatus 102, 104, 108 may carry out more sophisticated processing with respect to the measured exercise-related data on the basis of the received configuration data. For example, the portable apparatus 102, 104, 108 may calculate higher level exercise-related information from the measured data instead of simply forwarding the measured data to the wrist device for further processing. As the higher level calculations are carried out physically close to the exercise-measurement circuitries, even in the same housing, possible errors in conveying the measured data for further processing become minimized.

The configuration data comprises data for configuring the portable apparatus 102, 104, 108 such that the processing of exercise-related data is affected.

In an embodiment of the invention, the configuration data comprises user-related parameters which characterizes the user or are specific to the user. Examples of user-related parameters are name, physiological parameters such as age, weight, height, gender, body mass index, maximum performance capacity, activity parameter, previous energy expenditure parameters maximum heart rate.

In an embodiment of the invention, the configuration data comprises exercise-guidance parameters, such as energy expenditure target, heart rate zones, activity zones, anaerobic threshold, fitness classification identifier and/or dehydration warning limits. The heart rate or activity zones typically present limits within which a person shall exercise in order to reach a desired training effect. The fitness classification identifier characterizes the user's physical condition as a maximum performance capacity (VO2max), for example.

In an embodiment of the invention, the advanced exercise-related data comprises heart rate distribution information. Let us assume that the exercise is divided into three heart rate zones, i.e. a first zone, a second zone and a third zone. The heart rate distribution information in this case comprises the accumulated time in each zone the user spent during the exercise.

The user interface apparatus may be the wrist device 106 or another corresponding user interface device worn by the user. However, the user interface apparatus is not limited to that, and it may be a personal computer, a laptop, a personal digital assistant, a mobile phone, or another computer device comprising a user interface for presenting the exercise-related measurement data to the user and for applying configuration data to the portable apparatus 102, 104, 108. The user interface apparatus comprises a communication circuitry 222 configured to provide a bidirectional wireless communication connection with the portable apparatus 102, 104, 108. The user interface apparatus further comprises a user interface 228 enabling interaction with a user of the user interface apparatus. The user interface 228 may comprise display and input means as listed above. The user interface apparatus further comprises a processing circuitry 226 configured to communicate with the portable apparatus 102, 104, 108 through the communication circuitry 222 so as to receive processed exercise-related measurement data from the portable apparatus 102, 104, 108, to present the received processed exercise-related measurement data to the user, to receive configuration data from the user through the input means, and to cause transmission of the configuration data to the portable apparatus 102, 104, 108.

In an embodiment, the processing circuitry is implemented with a digital signal processor, a microcontroller, or another similar controller configurable by computer programs. The user interface apparatus may further comprise a memory 224 for storing such computer programs to be executed by the processing circuitry. An embodiment provides a computer program 232 comprising program instructions 234 which, when loaded into the user interface apparatus 106, cause the user interface apparatus 106 to carry out user interface and communication operations so as to present information received from the portable apparatus 102, 104, 108 to the user and to receive user inputs and forward the user inputs as the configuration data to the portable apparatus 102, 104, 108.

The computer program 232 may be in source code form, object code form, or in some intermediate form. The computer program 232 may be stored in the memory 224 or on a carrier 230 which may be any entity or device capable of carrying the program to the user interface apparatus 102. The carrier 230 may be a computer-readable storage medium. Besides this, the carrier 230 may be implemented as follows, for example: the computer program 232 may be embodied on a record medium, stored in a computer memory, embodied in a read-only memory, carried on an electrical carrier signal, carried on a telecommunications signal, and/or embodied on a software distribution medium. In some jurisdictions, depending on the legislation and the patent practice, the carrier 230 may not be the telecommunications signal.

There are many ways to structure the program 232. The operations of the program may be divided into functional modules, sub-routines, methods, classes, objects, applets, macros, etc., depending on the software design methodology and the programming language used. In modern programming environments, there are software libraries, i.e. compilations of ready-made functions, which may be utilized by the program for performing a wide variety of standard operations.

Figure 3:
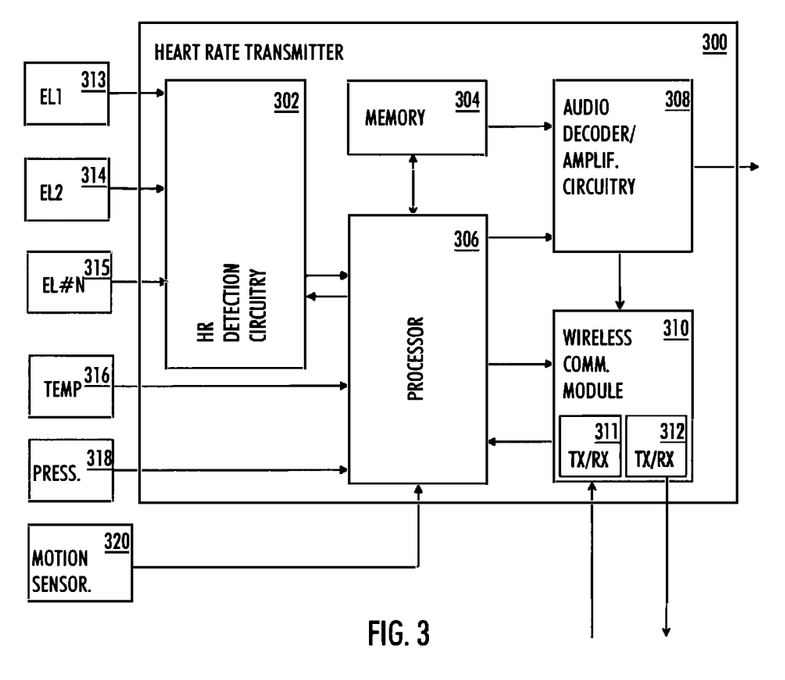
FIG. 3 is a block diagram of a portable apparatus according to an embodiment of the invention.

Let us now consider the portable apparatus carrying out the measurements and processing the measured data on the basis of the configuration data received over the wireless communication connection. FIG. 3 illustrates a more detailed block diagram of an embodiment of the portable apparatus, now in the form of a heart activity sensor 300. A typical heart activity sensor 300 further includes support structure not shown which enables the user to attach the heart activity sensor 300 to his body, such as chest.

The heart activity sensor 300 may also include other sensors, as described in greater detail below. The heart activity sensor 300 receives measured heart-rate activity (ECG) signals from two or more electrodes 313, 314, 315 in contact with the user's body. The electrodes 313 to 315 may be conventional electrodes commonly used in connection with training applications. The heart activity sensor 300 comprises a heart rate detection circuitry 302 configured to detect pulses (peaks) in the signal(s) received from the electrode(s) 313 to 315.

In an embodiment of the invention, the heart rate detection circuitry 302 detects signatures, such as P, Q, R S and/or T wave from the EKG. The heart-rate detection circuitry may also filter the received signals according to determined filtering parameters so as to improve the accuracy of the pulse detection. Then, the heart-rate detection circuitry outputs detected pulse rate information to a processor 306 configured to calculate higher level exercise-related information from the pulse rate information on the basis of configuration data retrieved from a memory 304.

In an embodiment, the heart activity sensor 300 receives exercise-related measurement data from other sensors, such as a temperature sensor 316 measuring ambient or body temperature, a pressure sensor 318 measuring pressure, and/or a motion sensor 320 measuring user's motions. In this context the pressure sensor 318 and temperature sensor 316 may be referred to as a thermodynamic sensor.

The processor 306 may be configured to calculate higher level exercise-related information from the exercise-related measurement data received from such sensors on the basis of configuration data retrieved from a memory 304. The connection between the heart activity sensor 300 and the sensors 313 to 320 may be wired or wireless. The sensor(s) may even be disposed in the same housing as the heart activity sensor 300.

In the wireless embodiment, a sensor providing the measured data may include a transmitter configured to process the measured data into electromagnetic radiation, and the heart activity sensor 300 may comprise a receiver adapted to receive the electro-magnetic radiation from the sensor and to process the received electromagnetic radiation into a form suitable for further processing. The heart activity sensor 300 may also include a clock or a timer for counting time and duration of the exercise and to enable exercise guidance.

The processor 306 is in an embodiment realized by an ASIC (application-specific integrated circuit), but it can be foreseen that the processor is realized by a digital signal processor, a microcontroller, or any other suitable processing unit selected according to required processing capacity, power consumption, etc. When the processor is a digital signal processor of any kind, the heart activity sensor 300 may include one or more analog-to-digital converters converting the exercise-related measurement data output by the sensors 313 to 320 into a digital form. Such a digital signal processor may be configured by one or more computer programs. The memory 304 may store such computer programs to be executed by the processor 306. An embodiment provides a computer program comprising program instructions which, when loaded into the processor 306, cause the processor 306 to carry out signal processing operations so as to calculate higher level exercise-related data from the measurement data provided by the sensors, wherein the calculation is based on the configuration data stored in the memory 304. The above discussion related to the properties of such computer programs and their carriers applies here, too.

As described above, the heart activity sensor 300 receives the configuration data over a bidirectional wireless communication connection from the user interface apparatus. The heart activity sensor 300 comprises a wireless communication module 310 (corresponding to the communication circuitry described above) so as to enable the bidirectional wireless communication connection. The bidirectional wireless communication connection refers to a connection that transfers payload data to both directions, i.e. not just radio-link specific control signaling. The wireless communication module 310 may be configured to operate a single bidirectional wireless communication link realized according to the specifications of Bluetooth (or Bluetooth low energy), wireless USB (Universal Serial Bus) or Zigbee (IEEE 802.15.4). The bidirectional connection may even utilize wireless local area network (IEEE 802.11x) or mobile telecommunication technology, such as GSM or UMTS. In the case of GSM and UMTS (or another mobile telecommunication system utilizing fixed public radio access network infrastructure, the configuration data may be input via a text message (SMS) or through a packet radio connection, e.g. GPRS, EDGE, W-CDMA, HSDPA/HSUPA, etc. known in the field of mobile telecommunications.

Alternatively, the wireless communication module 310 may include at least two communication link modules 311 and 312, wherein a first communication link module 311 is configured to transmit the processed higher-level exercise-related measurement information (and other information) to the user interface apparatus, and a second communication link module 312 is configured to receive the configuration data from the user interface apparatus. The first communication link module 311 may be dedicated for transmission only, and it may be configured to carry out the transmission according to Bluetooth (or Bluetooth low energy), ANT, W.I.N.D, Zigbee, or inductive-based technology. The second communication link module 312 may be dedicated for reception only, and it may be configured to carry out the reception according to Bluetooth (or Bluetooth low energy), Zigbee, wireless USB, or any other suitable wireless communication technology.

In an embodiment, the inductive-based technology is based on at least one of the following frequencies: 27 kHz, 125 kHz, 131 kHz, 250 kHz, and below 10 kHz, such 5 kHz.

In an embodiment, both first and second communication link module 311 and 312 are configured to establish bidirectional wireless links but to different user interface devices. The user may, for example, wear a wrist device described above and a headset, and the first communication link module 311 may be configured to establish a first bidirectional wireless communication link to the wrist device for presenting processed exercise-related data and for receiving the configuration data. The second communication link module 312 may be configured to establish a second bidirectional wireless communication link to the headset for playing audible processed exercise-related data (or other audio) and for receiving the configuration data. In the latter case, the headset may include a microphone and a voice-recognition algorithm to detect voice commands provided by the user and to forward the voice commands to the heart activity sensor 300 as the configuration data.

In another embodiment, the heart activity sensor is configured to establish a first and a second wireless communication links, wherein the first link is used to convey control parameters controlling the operation of the second link. The control parameters conveyed through the first link may include transmission power control parameters, modulation and/or coding parameters. Then, the heart activity sensor comprised by the portable apparatus may control transmission parameters of the second link on the basis of control parameters received through the first link. However, the first link primary configured for transmission of the payload data may also be used for transferring the advanced exercise-related data and/or the configuration data.

In an embodiment, the received configuration data includes exercise-related parameters, and the processor 306 is configured to process the received exercise-related measurement data by calculating the higher level exercise-related information from the received exercise-related measurement data on the basis of the received configuration data. The processor 306 may be configured to carry out at least one of an activity calculation algorithm, an energy expenditure calculation algorithm, a motion level algorithm, a fitness test algorithm, and a heart rate limits estimation algorithm. In order to enable the execution of such algorithms, the processor 306 receives additional parameters as the configuration data through the wireless communication module 310. Such parameters may include characteristics of the user and/or the training, and the parameters may be stored in association with a given user profile into the memory 304 for use by the algorithms. The memory 304 may store a plurality of user profiles of a group using the same heart activity sensor. Each user profile may specify user-specific parameters relating to the user of the heart activity sensor.

The processor 306 may also store in the memory measured data received from the one or more sensors listed above. The processor may accumulate a determined amount of measured data before calculating the further exercise information from the measured data. Such measured data stored in the memory may include single- or multi-channel ECG, temperature, ambient pressure, motion data in the form of acceleration versus time. The processor may also calculate some information derivable directly from the measured data without external configuration data, e.g. heart rate values, heart rate variability, RR intervals (duration between two consecutive R waves of the ECG), generic dehydration state calculated from the temperature, travel distance calculated from the motion data, motion analysis related to a swimming or running style, for example, mechanical training load based on the motion only without user-specific parameters etc.

Figure 4:
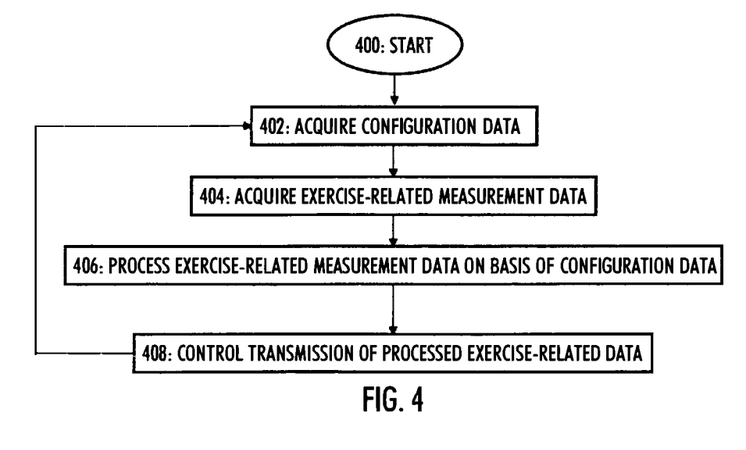
FIG. 4 is a flow diagram illustrating method for processing exercise-related measurement data according to an embodiment of the invention.

FIG. 4 illustrates a process for calculating higher level exercise related information from the measured data and the configuration data. The process may be carried out in the portable apparatus according to embodiments of the invention. Referring to FIG. 4, the process starts in block 400. In block 402, the configuration data is acquired. The configuration data is received as a user input from the user interface device over a wireless communication link and stored in the memory for acquisition. The configuration data may include user-specific parameters and/or exercise-guidance parameters defining the guidance or instructions for the exercise to be conducted by the user. In practice, not all the user-specific and/or exercise-guidance parameters need to be conveyed over the wireless link every time the exercise is started. Such parameters may have been transferred to the portable apparatus beforehand when the user has set up the system. The user may simply identify himself/herself through the user interface input and optionally input the type of exercise he/she wishes to carry out. The user interface apparatus then conveys according information to the portable apparatus over the wireless link. In response to the reception of the user and exercise identification data, the portable apparatus may acquire corresponding user-related parameters and exercise guidance parameters from the memory. The portable apparatus activates and/or deactivates sensors on the basis of the type of exercise to be conducted in order to disable unnecessary sensors and save battery power.

In block 404, exercise-related measurement data is acquired directly from the sensors and/or from the memory. The measurement data may include raw measurement data received from the sensors and/or processed data such as the heart rate and/or heart rate variability. In block 406, the higher level exercise-related information is calculated on the basis of the measurement data acquired in block 404 and the configuration data acquired in block 402. Next, a few examples of the advanced exercise related data is listed.

In an embodiment, energy expenditure is calculated by using the heart rate as the measurement data and age, gender, weight, height, and a fitness index as the user-related configuration data. In this case, the advanced exercise-related data includes energy expenditure data. The energy expenditure data may include the total energy expenditure during a specific exercise, energy expenditure rates during exercise, energy expenditure in metabolic component levels, such as fats, carbohydrates and/or proteins.

In an embodiment, fitness parameters (e.g. VO2max value known also as maximal oxygen uptake) are calculated by using the heart rate and/or hearty rate variability as the measurement data and age and gender as the configuration data. In this case, the advanced exercise-related data comprises a fitness parameter. The fitness parameter may presented in any unit, such as activity unit, from which a fitness parameter may be derived. An example of relating activity and fitness parameter is a Jackson formula, which provides a relationship between the maximum oxygen uptake and estimated physical activity.

In an embodiment, a relaxation estimate is calculated by using the heart rate variability or a parameter proportional to the heart rate variability as the measurement data. In this case, the advanced exercise-related data includes a relaxation estimate. The relaxation estimate may also be calculated from the power spectrum of the ECG. In an embodiment of the invention, a relaxation estimate may is obtained from the trend of heart rate value when a person is a in a recovery phase after high-load exercise phase. The relaxation estimate may characterize the physical or mental relaxation of a person.

In an embodiment, training load is calculated on the basis of mechanical stress derived by using the motion data, cardiovascular training load derived by using the heart rate, and/or pressure information (indicating air/water pressure) as the measurement data and age, gender, and weight as the configuration data. The training load characterizes the effect of the training in terms of physical load and the resulting need for recovery. In this case, the advanced exercise-related data includes training load parameter or associated recovery need parameter.

In an embodiment, user-specific heart rate zones, such as that based on heart rate variability, are calculated by using the heart rate as the measurement data and age, gender, and fitness classification as the configuration data.

In an embodiment, recovery estimate is calculated by using the heart rate variability as the measurement data. In this case, the advanced exercise-related data comprises the recovery estimate. A recovery estimate is a parameter which characterizes the user's recovery status. The recovery estimate may be presented by time required for a desired level of recovery. In an embodiment, the recovery status is presented in a form of exercise instruction which is may be given in time required to a predetermined recovery state.

In an embodiment, a dehydration estimate is calculated by using the heart rate and the temperature as the measurement data and possibly age, gender, weight and/or height as the configuration data. In this case, the advanced exercise-related data comprises a dehydration estimate. The dehydration estimate may be presented with the amount of beverage or beverage component, such as water or sodium, required to obtain a desired hydration state. In an embodiment, the temperature sensor 316 and heart rate sensor 300 are used in the portable apparatus 102, 104, 108.

Other algorithms known in the field of exercise-related algorithms may be calculated in block 406 as well. Block 406 may also (or alternatively) include comparison of the (processed) measurement data with exercise-guidance parameters received as the configuration data. The current heart rate may be compared with heart rate targets defined as the configuration data for the workout. Other measurement data or higher level exercise-related data calculated in block 406 may be compared with corresponding targets received as the configuration data so as to determine whether or not the workout follows the predetermined instructions. In these cases, the advanced exercise-related data comprises indication signals that carry information on the state of the current exercise relative to the data comprised by the configuration data. The indication signal may give rise to audible or visible alarm in the user interface apparatus 102,104,108.

In block 408, transmission of the exercise-related data or other data to the user interface apparatus is controlled. The exercise-related data transmitted to the user interface apparatus may include higher-level information calculated in block 406 or other exercise-related information.

The exercise-related information transmitted in block 408 may include information transmitted periodically on a continuous basis during the exercise, e.g. energy expenditure, heart rate, heart rate variability, temperature, travel speed and/or distance, relaxation estimate, fitness parameter, exercise zone status, current training load (mechanical, cardiovascular, their combination or both), and dehydration state. The interval between successive transmissions may be 1 second, but the transmission interval may be adjustable parameter.

The exercise-related information transmitted in block 408 may also include information transmitted once after the workout, such as ECG, RR data, motion sensor data as the function of time, etc. As the other information, system information, such as memory status, processing status, etc. may be transmitted automatically or upon a request received from the user interface apparatus in response to the user input. Any exercise-related information calculated in block 406 may also be transmitted in block 408 only in response to the request received over the wireless communication link from the user interface apparatus.

Additionally, control information controlling the exercise may be transmitted in block 408 in response to the operations carried out in block 406. For example, if in block it has been determined that the current heart rate is not within the current target heart rate limits (in the appropriate heart rate zone), a corresponding notification may be sent in block 408 to notify the user to either increase or decrease training load. In response to the reception of such a message, the user interface apparatus displays appropriate icon in the display and/or plays appropriate sounds through a loudspeaker so as to instruct the user.

In an embodiment, the configuration data includes sensor filtering data controlling the heart-rate detection circuitry 302 or another corresponding circuitry carrying out pre-processing of signals provided by one or more of the sensors 313 to 320 listed above. As mentioned above, the heart-rate detection circuitry filters the electric measurement signals provided by the electrodes 313 to 315 so as to improve the detection accuracy. The filtering parameters may be adaptive, and different filtering parameters may be used according to a given criterion, e.g. ambient conditions (temperature), exercise type (running, cycling, roller skating) etc. As a consequence, the filtering parameters may be input from the user interface apparatus as a configuration data and applied to the heart-rate detection circuitry so as to carry out the filtering according to the filtering parameters. The filtering parameters may control the heart-rate detection circuitry 302 to implement a specific physical filtering circuitry.

In an embodiment, the processing capacity of the wireless communication module 310 is utilized in the calculation of the higher-level exercise-related information. The capacity of the wireless communication module 310 may be oversized or it may be in use only occasionally and, thus, the processor 306 of the portable apparatus may monitor the loading of the wireless communication module 310, e.g. its modem processor, and assign computation operations and/or sub-routines to the wireless communication module 310 when it detects that there is processing capacity available in the wireless communication module 310. The processor 306 may instruct the wireless communication module 310 to execute the computation of any one of the above-listed higher-level computations or a sub-routine of such a computation.

As mentioned above, the portable apparatus according to embodiments of the invention may be the heart activity sensor in contact with the user's body for heart-rate measurement, the stride sensor attached to the user's shoe, the positioning device attachable to the arm of the user, a bike sensor attached to the bike, a swimming sensor attachable to the arm of the user, or a hybrid of any of the device listed above.

The portable apparatus processes the exercise-related measurement data so as to derive higher-level exercise-related information on the basis of the configuration data received from the user interface apparatus over the bidirectional wireless connection. The portable device itself may be provided with no user interface at all, and the user interaction is carried out through the user interface apparatus over the bidirectional wireless connection. However, the invention should not be limited to the devices with no user interface and, actually, an embodiment with the user interface is described below.

The portable apparatus receives the configuration data from the user interface apparatus and transmits the advanced exercise-related information to the user interface apparatus. The actual payload data transferred between the portable apparatus and the user interface apparatus may be designed in various manners. For example, the portable apparatus may transmit the advanced exercise-related information to the user interface apparatus in binary values defining the proportions of the different types of the exercise-related information. The transferred values are associated with the corresponding types of the exercise-related information, e.g. the values may be provided in dedicated fields of the transferred messages.

In another embodiment, the advanced exercise-related data comprises low-level raw data, such as pixel values of a display unit, thereby controlling the user interface apparatus to display the exercise-related data.

Referring now back to FIG. 3, in an aspect of the invention, the portable apparatus comprises an audio decoder and audio playback circuitry 308, and the configuration data received from the user interface apparatus may be control data controlling the playback and operation of the audio decoder and playback circuitry 308. The audio decoder may be an MPEG-1 Layer 3 (MP3) decoder, a Windows Media Audio decoder, or any other audio decoder known in the art and configured to decode and extract encoded and compressed audio tracks stored in the memory 304. The memory 304 storing the audio tracks may be the same physical non-volatile memory circuitry used in connection with other operations of the portable apparatus, or the audio tracks may be stored in an external, detachable memory unit, e.g. a memory card (SD, Memory stick, or another type of flash memory). The audio playback circuitry 308 may include an audio signal amplifier to amplify the decoded audio tracks and an audio output interface to output the audio tracks being played. The audio output interface may be realized by wired headphone connections known in the art, and/or the audio output interface may utilize the wireless communication module 310 to provide the audio output to Bluetooth-equipped headphones, for example. The portable apparatus may also transmit audio playback information to the user interface apparatus, e.g. the wrist device, over the wireless bidirectional connection so as to display the playback information to the user. The playback information may include the name of an audio track currently played, an artist, playback duration (elapsed time and/or remaining time), the next song, a playlist, MP3 metadata, etc. The configuration data received from the user interface apparatus over the wireless connection may include control data indicating the playback of the next track, activation/disabling the music playback, volume control data, etc. Additionally, the portable apparatus may include wired means for transferring the audio tracks into the memory. Such means may include a universal serial bus (USB) interface. The USB interface may also be used for recharging a battery (not shown) of the portable apparatus.

In an embodiment where at least some of the components of the portable apparatus, e.g. the processor 306, the audio decoder 308, and/or the wireless communication module, are controlled by software, a software update is applied to the portable apparatus as the configuration data from the user interface apparatus. The software update may be transferred to the portable apparatus over the bidirectional wireless communication link and, upon completion of the transfer, the portable apparatus is configured to carry out the software version upgrade. In another embodiment, the software upgrade is carried out through the wired USB connection.

As used in this application, the term 'circuitry' refers to all of the following: (a) hardware-only circuit implementations, such as implementations in only analog and/or digital circuitry, and (b) to combinations of circuits and software (and/or firmware), such as (when applicable): (i) a combination of processor(s) or (ii) portions of processor(s)/software including digital signal processor(s), software, and memory (memories) that work together to cause an apparatus to perform various functions, and (c) to circuits, such as a microprocessor(s) or a portion of a microprocessor(s), that require software or firmware for operation, even if the software or firmware is not physically present.

This definition of 'circuitry' applies to all uses of this term in this application. As a further example, as used in this application, the term "circuitry" would also cover an implementation of merely a processor (or multiple processors) or portion of a processor and its (or their) accompanying software and/or firmware. The term "circuitry" would also cover, for example and if applicable to the particular element, a baseband integrated circuit or applications processor integrated circuit for a mobile phone or a similar integrated circuit in server, a cellular network device, or other network device.

It should be noted that while the Figures illustrate various embodiments of the portable apparatus and the user interface apparatus, they are simplified block diagrams that only show some elements and functional entities, all being logical units whose implementation may differ from what is shown. The connections shown in these figures are logical connections; the actual physical connections may be different. Interfaces between the various elements may be implemented with suitable interface technologies. It is apparent to a person skilled in the art that the described apparatuses may also comprise other functions and structures. It should be appreciated that details of some functions, structures, and elements, and the protocols used for communication are irrelevant to the actual invention. Therefore, they need not be discussed in more detail here, because such discussion might blur the invention with unnecessary details. The implementation and features of the apparatuses according to the invention develop rapidly. Such development may require extra changes to the embodiments described above. Therefore, all words and expressions should be interpreted broadly and they are intended to illustrate, not to restrict, the embodiments. Although the apparatuses have been depicted as separate single entities, different parts may be implemented in one or more physical or logical entities. It will be obvious to a person skilled in the art that, as technology advances, the inventive concept can be implemented in various ways. The invention and its embodiments are not limited to the examples described above but may vary within the scope of the claims.

What is claimed is:

1. A portable apparatus comprising:
   one or more exercise-measurement circuitry configured to measure exercise-related measurement data related to a user carrying out an exercise;
   a communication circuitry configured to provide the portable apparatus with wireless communication capability; and
   a processing circuitry configured to perform operations comprising:
      receiving the exercise-related measurement data from the one or more exercise-measurement circuitry;
      receiving configuration data from an external user interface apparatus over a bidirectional wireless communication connection established through the communication circuitry, wherein the bidirectional wireless communication connection is capable of transferring payload data in both directions, wherein the received configuration data includes exercise-related parameters;
      processing the exercise-related measurement data according to the received exercise-related parameters in order to obtain advanced exercise-related data; and
      communicating the advanced exercise-related measurement data to the user interface apparatus over the bidirectional wireless communication connection, wherein the configuration data further comprises a type of the exercise to be conducted, and wherein the processing circuitry is configured to activate and/or deactivate the one or more exercise-measurement circuitry based on the type of the exercise to be conducted.

2. The apparatus of claim 1, wherein the advanced exercise-related data processed by the processing circuitry comprises at least one of energy expenditure data and performance capacity data.

3. The apparatus of claim 1, wherein the processing circuitry is further configured to process the exercise-related measurement data on the basis of at least one of the following configuration data received from the user interface apparatus: user-related parameters describing characteristics of the user, wherein the exercise-related parameters include defining instructions or guidance for the exercise to be conducted, and filtering parameters configuring filtering of the received exercise-related measurement data.

4. The apparatus of claim 1, wherein the one or more exercise-measurement circuitry includes at least one of the following sensors: a thermodynamic sensor, a motion sensor, wherein the received configuration data includes exercise-related parameters, and wherein the processing circuitry is further configured to process measurement data received from the at least one of the thermodynamic sensor and motion sensor by calculating the advanced exercise-related data from the received measurement data on the basis of the received configuration data.

5. The apparatus of claim 1, wherein the communication circuitry is further configured to perform operations comprising:
   establishing a first wireless communication link and a second wireless communication link to the user interface apparatus to form the bidirectional wireless communication connection; and operating the first wireless communication link and the second wireless communication link in parallel by using the first wireless communication link for controlling the operation of the second wireless communication link.

6. The apparatus of claim 1, further comprising:
a memory unit configured to store audio tracks;
an audio decoder comprised in the processing circuitry and configured to decode at least one of the audio tracks stored in the memory and to play the at least one decoded audio track; and
audio output means to output the at least one audio track being played, wherein the playback of the at least one audio track is operative on the basis of the received configuration data, and wherein the processing circuitry is further configured to transmit data related to the audio track being played to the user interface apparatus via the bidirectional wireless communication connection.

7. The apparatus of claim 1, wherein the one or more exercise-measurement circuitry is configured to measure exercise-related measurement data that characterizes the user's heart activity.

8. A method of processing exercise-related measurement data in a portable apparatus, the method comprising:
acquiring exercise-related measurement data by using one or more exercise-measurement circuitry;
establishing a bidirectional wireless communication connection capable of transferring payload data to both directions through a communication circuitry of the portable apparatus with an external user interface apparatus;
receiving configuration data in the portable apparatus from the external user interface apparatus over the bidirectional wireless communication connection, wherein the received configuration data includes exercise-related parameters;
processing the exercise-related measurement data on the basis of the received exercise-related parameters, with processing circuitry of the portable apparatus, in order to obtain advanced exercise-related data; and
causing transmission of the advanced exercise-related measurement data to the user interface apparatus over the bidirectional wireless communication connection, wherein the configuration data further comprises a type of the exercise to be conducted, the method further comprising activating and/or deactivating, by the processing circuitry, the one or more exercise measurement circuitry on the basis of the type of the exercise to be conducted.

9. The method of claim 8, wherein the advanced exercise-related data comprises at least one of energy expenditure data and performance capacity data.

10. The method of claim 8, further comprising processing the exercise-related measurement data on the basis of at least one of the following configuration data received from the user interface apparatus: user-related parameters describing characteristics of the user, wherein the exercise-related parameters include defining instructions or guidance for the exercise to be conducted, and filtering parameters configuring filtering of the received exercise-related measurement data.

11. The method of claim 8, further comprising:
establishing a first wireless communication link and a second wireless communication link to the user interface apparatus to form the bidirectional wireless communication connection; and
operating the first wireless communication link and the second wireless communication link in parallel by using the first wireless communication link for transmission of the advanced exercise-related measurement data and the second wireless communication link for reception of the configuration data.

12. The method of claim 8, further comprising:
storing audio tracks in a memory unit;
decoding at least one of the audio tracks stored in the memory;
operating playback of the at least one decoded audio track through audio output means, wherein the playback of the at least one audio track is operative on the basis of the received configuration data, and
transmitting data related to the audio track being played to the user interface apparatus over the bidirectional wireless communication connection.

13. A non-transitory computer-readable medium comprising instructions encoded thereon that, when executed by a processing device, perform operations comprising:
acquiring exercise-related measurement data by using one or more exercise-measurement circuitry;
establishing a bidirectional wireless communication connection capable of transferring payload data to both directions through a communication circuitry of the processing device with an external user interface apparatus;
receiving configuration data from the external user interface apparatus over the bidirectional wireless communication connection, wherein the received configuration data includes exercise-related parameters;
processing the exercise-related measurement data on the basis of the received exercise-related parameters in order to obtain advanced exercise-related data; and
causing transmission of the advanced exercise-related measurement data to the user interface apparatus over the bidirectional wireless communication connection, wherein the configuration data further comprises a type of the exercise to be conducted, and the operations further include activating and/or deactivating the one or more exercise-measurement circuitry on the basis of the type of the exercise to be conducted.

14. A system that processes exercise-related measurement data, the system comprising:
a portable apparatus comprising:
one or more exercise-measurement circuitry configured to measure exercise-related measurement data related to a user carrying out an exercise;
a communication circuitry configured to provide the portable apparatus with wireless communication capability; and
a processing circuitry configured to perform operations comprising:
receiving the exercise-related measurement data from the exercise-measurement circuitry;
receiving configuration data from an external user interface apparatus over a bidirectional wireless communication connection established through the communication circuitry, wherein the bidirectional wireless communication connection is capable of transferring payload data in both directions, wherein the received configuration data includes exercise-related parameters;

processing the exercise-related measurement data according to the received exercise-related parameters in order to obtain advanced exercise-related data; and communicating the advanced exercise-related measurement data to the user interface apparatus over the bidirectional wireless communication connection, wherein the configuration data further comprises a type of the exercise to be conducted, and wherein the processing circuitry is configured to activate and/or deactivate the one or more exercise-measurement circuitry based on the type of the exercise to be conducted; and the user interface apparatus comprising:
an additional communication circuitry configured to provide the bidirectional wireless communication connection with the portable apparatus;
a user interface enabling interaction with the user; and
an additional processing circuitry configured to communicate with the portable apparatus through the communication circuitry so as to receive the advanced exercise-related measurement data from the portable apparatus, to present the received advanced exercise-related measurement data to the user via the user interface, to receive configuration data from the user via the user interface, and to cause transmission of the configuration data to the portable apparatus.

* * * * *